United States Patent
Wang et al.

(10) Patent No.: US 9,693,963 B2
(45) Date of Patent: Jul. 4, 2017

(54) 2,2',6,6'-TETRAISOPROPYL-4,4'-2-BIPHENOL SOFT CAPSULE AND METHOD FOR PREPARING SAME

(75) Inventors: Rutao Wang, Shaanxi (CN); Long An, Shaanxi (CN); Huijing Hu, Shaanxi (CN); Shupan Guo, Shaanxi (CN); Tao Chen, Shaanxi (CN); Weijiao Wang, Shaanxi (CN)

(73) Assignee: Xi'an Libang Pharmaceutical Co., Ltd., Shaanxi (CN)

( * ) Notice: Subject to any disclaimer, the term of this patent is extended or adjusted under 35 U.S.C. 154(b) by 0 days.

(21) Appl. No.: 14/412,296

(22) PCT Filed: Aug. 2, 2012

(86) PCT No.: PCT/CN2012/079589
§ 371 (c)(1),
(2), (4) Date: Feb. 5, 2015

(87) PCT Pub. No.: WO2014/005363
PCT Pub. Date: Jan. 9, 2014

(65) Prior Publication Data
US 2015/0352052 A1     Dec. 10, 2015

(30) Foreign Application Priority Data
Jul. 2, 2012   (CN) .......................... 2012 1 0224673

(51) Int. Cl.
A61K 31/355 (2006.01)
A61K 9/48 (2006.01)
A61K 31/05 (2006.01)

(52) U.S. Cl.
CPC .............. *A61K 9/48* (2013.01); *A61K 9/4858* (2013.01); *A61K 31/05* (2013.01); *A61K 31/355* (2013.01)

(58) Field of Classification Search
None
See application file for complete search history.

(56) References Cited

U.S. PATENT DOCUMENTS

| 6,248,771 B1 * | 6/2001 | Shenoy ................ A61K 9/0019 514/418 |
| 2005/0192340 A1 * | 9/2005 | Flashner-Barak ... A61K 9/4858 514/423 |
| 2011/0212170 A1 * | 9/2011 | Ditzinger ............. A61K 9/4858 424/456 |

FOREIGN PATENT DOCUMENTS

| CN | 101804043 A | 8/2010 |
| CN | 102475770 A | 5/2012 |
| CN | 102716103 A | 10/2012 |
| JP | 2000-095676 A | 4/2000 |
| JP | 2007-513097 | 4/2007 |

OTHER PUBLICATIONS

Machine english translation of IDS document CN101804043, no date available.*
International Search Report and Written Opinion for Application No. PCT/CN2012/079589 dated.
Office Action for Chinese Application No. 201210224673.6 dated Mar. 12, 2013.
Office Action from corresponding Japanese Patent Application No. 2015-518776 dated Mar. 22, 2016.
Office Action from corresponding Canadian Patent Application No. 2,880,945 dated Nov. 12, 2015.
Extended European Search Report from corresponding European Patent Application No. 12880562.9 dated Nov. 26, 2015.

* cited by examiner

*Primary Examiner* — Mina Haghighatian
*Assistant Examiner* — Erin Hirt
(74) *Attorney, Agent, or Firm* — Alston & Bird LLP

(57) ABSTRACT

Disclosed is a 2,2',6,6'-tetraisopropyl-4,4'-biphenol soft capsule composed of a capsule shell and the contents in the capsule, wherein the contents in the capsule include 2,2',6,6'-tetraisopropyl-4,4'-biphenol, a solvent, and an antioxidant, among others.

7 Claims, No Drawings

2,2',6,6'-TETRAISOPROPYL-4,4'-2-BIPHENOL SOFT CAPSULE AND METHOD FOR PREPARING SAME

FIELD OF INVENTION

The present invention belongs to the field of pharmaceutical formulations and relates to a novel formulation of 2,2',6,6'-tetraisopropyl-4,4'-biphenol, and in particular, to a soft capsule of 2,2',6,6'-tetraisopropyl-4,4'-biphenol.

BACKGROUND ART

In the current market, 2,2',6,6'-tetraisopropyl-4,4'-biphenol (hereinafter abbreviated as biphenol) is a compound against epileptic seizures recently developed by our company (see ZL 201010160034.9, titled "Use of biphenols and derivatives thereof as a medicament for treating epilepsy"). It can be used to treat many epileptic symptoms such as generalized tonic-clonic seizures (grand mal), absence seizures (petit mal), simple partial seizures, complex partial seizures (psychomotor seizures), and autonomic seizures (episodic seizures).

Experimental studies have shown that biphenol has very strong affinity with GABA receptors, has agonist activity for GABA and also antagonist activity for NMDA receptors, regulates $Ca^{2+}$ influx through $Ca^{2+}$ channels, and provides protection from excitotoxicity caused by kainic acid.

Since biphenol is a compound highly soluble in lipids, insoluble in water, and prone to oxidation, we have tried surfactants such as cyclodextrins, tween 80, VC, and DMSO to help dissolve or to solubilize biphenol, but find it difficult to achieve desirable results, which affects exploitation of the drug efficacy and limits clinical applications of biphenol.

In order to better exert the therapeutic effect of biphenol, current research has been focused on selecting a particular formulation suitable for biphenol, which is also an urgent demand of current clinical medicine.

SUMMARY OF INVENTION

We have conducted long-term research and surprisingly found that a soft capsule made with 2,2',6,6'-tetraisopropyl-4,4'-biphenol (abbreviated as biphenol throughout this specification) not only overcomes its drawback of poor solubility in water, but also allows for convenient oral administration and good bioavailability.

One of the objectives of the present invention is to provide a biphenol soft capsule which can not only improve the stability, bioavailability, and anti-epileptic effect of this drug, but also facilitate its storage and transportation.

Although soft capsules have long been known as a conventional means to overcome poor water-solubility of drugs, the problem the present invention aims to solve is to rationally create a formulation according in particular to the special physical and chemical properties of biphenol, so as to produce a safe, stable, and efficacious biphenol soft capsule. Such a soft capsule is obtained through creative efforts by the inventors and is non-obvious.

In general, soft capsules are made from a capsule shell and the contents to be encapsulated in the capsule through a soft capsule formation machine. Improvements in stability and efficacy of drugs are associated with not only the composition of the contents inside the capsules but also the materials for the capsule shell.

Considering that the phenolic hydroxyl groups in biphenol, the active ingredient of the present invention, are easily oxidized, we have conducted studies and surprisingly found that vitamin E and its derivatives are particularly suitable for anti-oxidation of biphenol, as addition of vitamin E and its derivatives on one hand improves stability of the formulation, and on the other hand unexpectedly enhances efficacy of the formulation.

In particular, addition of 5% to 10% of an antioxidant with respect to the weight of the contents in the capsules can ensure better stability of the drug in the formulation.

In accordance with one preferred embodiment of the present invention, the present invention provides a biphenol soft capsule characterized in that the contents inside the soft capsule comprise 1% to 30% of biphenol and 1% to 20% of an antioxidant with respect to the contents in the soft capsule.

The antioxidant is selected from vitamin E and its derivatives, preferably one or more of tocopherol, tocopheryl acetate, tocotrienol, and tocotrienols, particularly preferably tocopheryl acetate.

An objective of the present invention is to provide a biphenol soft capsule that is easy to prepare and convenient and safe to administer. The preferred dispersant according to the present invention can not only dissolve biphenol well, but also improve stability of biphenol.

In accordance with one preferred embodiment of the present invention, the present invention provides a biphenol soft capsule characterized in that the contents inside the soft capsule comprise biphenol, a dispersant, and an antioxidant in the following amounts based on the weight of the contents inside the capsule:
biphenol: 1% to 30%
the dispersant: 60% to 90%
the antioxidant: 1% to 20%.

The dispersant is preferably one or more of vegetable oils, medium-chain oils, or structured oils ("structured oils" in accordance with the present invention refer to oils obtained by random structural rearrangements of medium-chain fatty acids and long-chain fatty acids on the backbone of one single glycerol molecule through hydrolysis and re-esterification of these fatty acids at a high temperature with a catalyst present).

The vegetable oils are preferably one or a combination of more than one of *Perilla* oil, cottonseed oil, olive oil, soybean oil, peanut oil, safflower oil, and corn oil.

In order to further stabilize the soft capsule of the present invention, a preservative can also be added. The preservative is selected from one or more of sorbic acid, methyl sorbate, methyl p-hydroxybenzoate, ethyl p-hydroxybenzoate, and propyl p-hydroxybenzoate.

In accordance with one preferred embodiment of the present invention, the present invention provides a biphenol soft capsule characterized in that the contents inside the soft capsule comprise biphenol, a dispersant, an antioxidant, and a preservative in the following amounts based on the weight of the contents inside the capsule:
biphenol: 1% to 30%
a dispersant: 60% to 90%
an antioxidant: 1% to 20%
a preservative: 0 to 0.3%.

In accordance with one preferred embodiment of the present invention, a preservative can be added not only into the contents inside the capsule, but also into the capsule shell, both of which can effect to well improve the stability of the soft capsule.

Another objective of the present invention is to provide a capsule shell suitable for biphenol soft capsules, and the capsule shell may be simply selected from conventional materials for capsule shells in the art.

In accordance with one preferred embodiment of the present invention, the capsule shell of the present invention is composed of a gel material, a plasticizer, and a solvent, wherein the gel material is selected from arabic gum, carrageenan, and gelatin, preferably gelatin; the plasticizer is selected from one or more of glycerol, xylitol, sorbitol, and methyl sorbate; the solvent is selected from water; and the weight ratio between the components is preferably gel material:plasticizer:water=1:0.3 to 0.6:1.

In accordance with one preferred embodiment of the present invention, the capsule shell of the present invention consists of a gel material, a plasticizer, a preservative, and a solvent; and the weight ratio between the components is preferably gel material:plasticizer:preservative:water=1:0.3 to 0.6:0.005 to 0.05:1.

An objective of the present invention is to provide a method for preparing a biphenol soft capsule, comprising steps of:
(1) preparation of a capsule shell: taking a gel material and water in an appropriate amount and mixing them thoroughly; taking a plasticizer separately and mixing it thoroughly with an appropriate amount of water, melting this mixture by heating, then adding the prepared gel material solution thereto, heating the mixture under stirring to a molten state, followed by thorough mixing and evacuation, and maintaining the temperature until use;
(2) preparation of the contents to be encapsulated in the capsule: mixing biphenol with a dispersant and an antioxidant, adding a preservative thereto, heating the mixture to about 55° C. to 80° C. under protection of nitrogen gas, followed by thorough stirring until dissolved, and maintaining the temperature until use;
(3) preparation of a soft capsule: preparing a soft capsule from the contents to be encapsulated in the capsule and the material for the capsule shell as prepared above by using a soft capsule formation machine, followed by drying, to produce the biphenol soft capsule.

An objective of the present invention is to provide a method for preparing a biphenol soft capsule, comprising steps of:
(1) preparation of a capsule shell: taking a gel material and water in an appropriate amount and mixing them thoroughly; taking a plasticizer separately and mixing it thoroughly with an appropriate amount of water, melting this mixture by heating, then adding the prepared gel material solution thereto, adding a preservative thereto under stirring, heating the mixture to a molten state, followed by thorough mixing and evacuation, and maintaining the temperature until use;
(2) preparation of the contents to be encapsulated within the capsule: mixing biphenol with a dispersant and an antioxidant, heating the mixture to about 55° C. to 80° C. under protection of nitrogen gas, followed by thorough stirring until dissolved, and maintaining the temperature until use;
(3) preparation of a soft capsule: preparing a soft capsule from the contents to be encapsulated in the capsule and the material for the capsule shell as prepared above by using a soft capsule formation machine, followed by drying, to produce the biphenol soft capsule;
wherein, the temperature maintained in step (2) is preferably about 60° C. to 75° C.

The vegetable oil-based dispersant used in the present invention can well dissolve biphenol. Since the drug is completely dissolved in a digestible oil, a very safe formulation can be obtained. The dispersant can be rapidly digested into free fatty acids because of its biocompatibility, thereby providing high bioavailability and an excellent anti-epileptic effect.

Addition of vitamin E and its derivatives to the contents within the soft capsule of the present invention can structurally improve the stability of biphenol to a great extent. Moreover, and more importantly, the added vegetable oils form a composite solvent together with antioxidants like vitamin E to dissolve biphenol, so as to afford a stable liquid formulation of molecular biphenol.

An objective of the present invention is to provide use of a biphenol soft capsule for treating and combating various types of epileptic symptoms. The formulation is prepared for oral administration, and can be used to treat various epileptic symptoms such as generalized tonic-clonic seizures (grand mal), absence seizures (petit mal), simple partial seizures, complex partial seizures (psychomotor seizures), and autonomic seizures (episodic seizures). The soft capsule prepared in accordance with the present invention is prepared by a simple process with good stability, and can be conveniently administered and meet the safety requirements of clinical medication.

DETAILED DESCRIPTION

The examples below are intended to further illustrate the present invention, but by no means to limit the scope of the present invention. The present invention will be explained in detail with reference to the examples below. It will be understood by a person skilled in the art that the present invention is not limited to these examples and the preparation methods used. Furthermore, a person skilled in the art may make equivalent replacements, combinations, improvements, or modifications with respect to the present invention, which are all encompassed within the scope of the present invention.

Part I. Soft Capsules Prepared with Biphenol at Various Concentrations

Example 1. Soft Capsule with 20% Biphenol

| Biphenol | 100 g |
|---|---|
| Soybean oil | 350 g |
| Tocopheryl acetate | 50 g |
| Methyl p-hydroxybenzoate | 1 g |

1000 soft capsules in total were prepared.
Preparation Process:
1) preparation of the contents to be encapsulated within the capsule: mixing 100 g biphenol with 350 g soybean oil and 50 g tocopheryl acetate, adding 1 g methyl p-hydroxybenzoate thereto, heating the mixture to 70° C. under protection of nitrogen gas, followed by stirring until dissolved, and maintaining the temperature until use;
2) preparation of a capsule shell: weighing 100 g gelatin and an appropriate amount of water, and mixing them thoroughly; weighing 40 g glycerol separately and mixing it thoroughly with water, then adding the prepared gel material solution thereto, heating the mixture under stirring to a molten state, followed by thorough mixing and evacuation, and maintaining the temperature until use;
3) preparation of a soft capsule: preparing a soft capsule from the contents and the material for the capsule shell prepared above by using a soft capsule formation machine, followed by drying, to produce the biphenol soft capsule.

Example 2. Soft Capsule with 10% Biphenol

| | |
|---|---|
| Biphenol | 50 g |
| Corn oil | 400 g |
| Tocotrienol | 50 g |
| Ethyl p-hydroxybenzoate | 1 g |

1000 soft capsules in total were prepared.
Preparation Process:
1) preparation of the contents to be encapsulated within the capsule: mixing 50 g biphenol with 400 g corn oil and 50 g tocotrienol, heating the mixture to 70° C. under protection of nitrogen gas, followed by stirring until dissolved, and maintaining the temperature until use;
2) preparation of a capsule shell: weighing 100 g gelatin and an appropriate amount of water, and mixing them thoroughly; weighing 40 g glycerol separately and mixing it thoroughly with water, then adding the prepared gel material solution thereto, adding 1 g methyl p-hydroxybenzoate thereto under stirring, heating the mixture to a molten state, followed by thorough mixing and evacuation, and maintaining the temperature until use;
3) preparation of a soft capsule: preparing a soft capsule from the contents and the material for the capsule shell prepared above by using a soft capsule formation machine, followed by drying, to produce the biphenol soft capsule.

Example 3. Soft Capsule with 30% Biphenol

| | |
|---|---|
| Biphenol | 150 g |
| Soybean oil | 300 g |
| Tocopheryl acetate | 50 g |
| Propyl p-hydroxybenzoate | 1.5 g |

1000 soft capsules in total were prepared.
The preparation process was the same as in Example 1.

Example 4. Soft Capsule with 5% Biphenol

| | |
|---|---|
| Biphenol | 25 g |
| Corn oil | 450 g |
| Tocopherol | 25 g |
| Methyl p-hydroxybenzoate | 0.5 g |

1000 soft capsules in total were prepared.
The preparation process was the same as in Example 2.

Part II. Soft Capsules Prepared with Dispersants in Various Amounts

Example 5. Biphenol Soft Capsule with 60% Soybean Oil

| | |
|---|---|
| Biphenol | 60 g |
| Soybean oil | 180 g |
| Tocopherol | 60 g |
| Methyl p-hydroxybenzoate | 0.5 g |

1000 soft capsules in total were prepared.
The preparation process was the same as in Example 1.

Example 6. Biphenol Soft Capsule with 70% Safflower Oil

| | |
|---|---|
| Biphenol | 100 g |
| Safflower oil | 350 g |
| Tocopheryl acetate | 50 g |
| Ethyl p-hydroxybenzoate | 0.5 g |

1000 soft capsules in total were prepared.
The preparation process was the same as in Example 2.

Example 7. Biphenol Soft Capsule with 80% Corn Oil

| | |
|---|---|
| Biphenol | 75 g |
| Corn oil | 400 g |
| Tocopheryl acetate | 25 g |
| Propyl p-hydroxybenzoate | 1 g |

1000 soft capsules in total were prepared.
The preparation process was the same as in Example 1.

Example 8. Biphenol Soft Capsule with 90% *Perilla* Oil

| | |
|---|---|
| Biphenol | 30 g |
| *Perilla* oil | 450 g |
| Tocotrienol | 20 g |
| Methyl p-hydroxybenzoate | 0.5 g |

1000 soft capsules in total were prepared.
The preparation process was the same as in Example 2.

Part III. Soft Capsules Prepared with Antioxidants in Various Amounts

Example 9. Soft Capsule with 5% Vitamin E

| | |
|---|---|
| Biphenol | 50 g |
| Soybean oil | 425 g |
| Tocopheryl acetate | 25 g |
| Ethyl p-hydroxybenzoate | 1 g |

1000 soft capsules in total were prepared.
The preparation process was the same as in Example 1.

Example 10. Soft Capsule with 10% Vitamin E

| | |
|---|---|
| Biphenol | 100 g |
| Soybean oil | 350 g |
| Tocopherol | 50 g |
| Methyl p-hydroxybenzoate | 1 g |

1000 soft capsules in total were prepared.
The preparation process was the same as in Example 2.

Example 11. Soft Capsule with 20% Vitamin E

| | |
|---|---|
| Biphenol | 100 g |
| Corn oil | 300 g |
| Tocotrienol | 100 g |
| Ethyl p-hydroxybenzoate | 0.5 g |

1000 soft capsules in total were prepared.
The preparation process was the same as in Example 1.

Part IV. Soft Capsules Prepared with Preservatives in Various Amounts

Example 12. Soft Capsule with 0.3% Preservative

| | |
|---|---|
| Biphenol | 100 g |
| Corn oil | 350 g |
| Tocopheryl acetate | 50 g |
| Methyl p-hydroxybenzoate | 1.5 g |

1000 soft capsules in total were prepared.
The preparation process was the same as in Example 1.

Example 13. Soft Capsule with 0.1% Preservative

| | |
|---|---|
| Biphenol | 50 g |
| Corn oil | 400 g |
| Tocotrienol | 50 g |
| Ethyl p-hydroxybenzoate | 0.5 g |

1000 soft capsules in total were prepared.
The preparation process was the same as in Example 2.

Example 14. Soft Capsule without Preservative

| | |
|---|---|
| Biphenol | 50 g |
| Corn oil | 400 g |
| Tocopherol | 50 g |

1000 soft capsules in total were prepared.
The preparation process was the same as in Example 1.

Example 15. Soft Capsule with 1% Biphenol

| | |
|---|---|
| Biphenol | 5 g |
| Corn oil | 450 g |
| Tocopherol | 25 g |
| Methyl p-hydroxybenzoate | 0.5 g |

1000 soft capsules in total were prepared.
The preparation process was the same as in Example 2.

Example 16. Soft Capsule with 1% Vitamin E

| | |
|---|---|
| Biphenol | 50 g |
| Soybean oil | 425 g |
| Tocopherol | 5 g |
| Ethyl p-hydroxybenzoate | 1 g |

1000 soft capsules in total were prepared.
The preparation process was the same as in Example 1.

Test Example 1. Solubility of Biphenol in Medium-Chain Oils, Structured Oils, and Vegetable Oils Solubility of biphenol in medium-chain oils, structured oils, and vegetable oils was measured by a solubility measurement method. The results are shown below.

| Type of oils | Solubility of biphenol in oil (mg/g) |
|---|---|
| Perilla oil | 440 |
| Cottonseed oil | 420 |
| Olive oil | 370 |
| Soybean oil | 480 |
| Peanut oil | 420 |
| Safflower oil | 410 |
| Corn oil | 390 |
| Medium-chain oil | 340 |
| Structured oil | 330 |

Solubility of biphenol in all of the above oils is greater than 300 mg biphenol/g oil, with the highest solubility in soybean oil, i.e. 480 mg biphenol/g soybean oil.

Test Example 2. Anti-Oxidation Test

Since biphenol has phenolic hydroxyl groups and is easily degraded by oxidation, an antioxidant should be added in the formulation. The antioxidative effect of 5% tocopheryl acetate added in soybean oil was investigated. A 100 mg/g biphenol solution in oil was prepared, and accelerated degradation was carried out at 80° C. for 3 days. The results are shown below.

| | Conditions for Stability Test | Biphenol content (% of the labeled content) |
|---|---|---|
| Biphenol Soft Capsule | 0 h, not heated and not degraded | 99.56 |
| Biphenol Soft Capsule (without tocopheryl acetate) | Degradation at 80° C. for 72 h | 71.04 |
| Biphenol Soft Capsule (with 5% tocopheryl acetate) | Degradation at 80° C. for 72 h | 98.34 |

The results demonstrate that the biphenol soft capsule with 5% antioxidant showed nearly no decrease in content after the stability test, whereas the biphenol soft capsule without antioxidant showed a 30% decrease in content.

Test Example 3. Selection of the Antioxidant Concentration

We also undertook in-depth studies on the antioxidative effect of vitamin E (tocopheryl acetate) in the formulation of the present invention. Formulations at tocopheryl acetate concentrations of 0%, 1%, 5%, 10%, 20%, and 30% were investigated respectively by carrying out degradation at 80° C. for 3 days and HPLC assays (100 mg biphenol dissolved in 1 g soybean oil in the sample solutions). The results are shown below.

|  | Tocopheryl acetate concentration | Biphenol content (% of the labeled content) |
|---|---|---|
| Biphenol Soft Capsule | 0% | 70.39% |
| Biphenol Soft Capsule | 1% | 75.12% |
| Biphenol Soft Capsule | 2% | 81.3% |
| Biphenol Soft Capsule | 5% | 98.23% |
| Biphenol Soft Capsule | 10% | 99.31% |
| Biphenol Soft Capsule | 20% | 99.54% |
| Biphenol Soft Capsule | 30% | 99.52% |

The results show that vitamin E at a concentration of 5% or more produced a better antioxidative effect, and that the drug content did not change any more when the concentration exceeded 20%. Considering that it is inappropriate to use an excessive amount of vitamin E as an antioxidant, a concentration of 5% to 10% is recommended. Here, the concentration of vitamin E is calculated as (Vitamin E/soybean oil)*100%.

Test Example 4. Stability Tests on Biphenol Soft Capsules

1. Tests on Relevant Factors

Biphenol soft capsules were placed under a condition of a high temperature of 40° C., a condition of a high temperature of 60° C., a condition of high humidity (relative humidity: 90%±5%), and a condition of intense light (4500 lx±500 lx), respectively, for 10 days. Samples were taken on day 5 and day 10 for measurement. The results are shown below.

| Investigation conditions | Time (day) | Appearance of the contents in the capsule | Disintegration time (min) | Content (% of the labeled content) |
|---|---|---|---|---|
| High temperature 40° C. | 0 | Yellow oily liquid | 7.7 | 99.97 |
|  | 5 | Yellow oily liquid | 8.6 | 99.65 |
|  | 10 | Yellow oily liquid | 8.8 | 99.46 |
| High temperature 60° C. | 0 | Yellow oily liquid | 8.7 | 99.87 |
|  | 5 | Yellow oily liquid | 7.9 | 99.65 |
|  | 10 | Yellow oily liquid | 8.4 | 99.13 |
| High humidity 90% ± 5% | 0 | Yellow oily liquid | 8.9 | 99.96 |
|  | 5 | Yellow oily liquid | 6.8 | 99.78 |
|  | 10 | Yellow oily liquid | 7.6 | 99.67 |
| Irradiation with intense light | 0 | Yellow oily liquid | 8.6 | 99.89 |
|  | 5 | Yellow oily liquid | 9.1 | 99.91 |
|  | 10 | Yellow oily liquid | 8.3 | 99.83 |

The above results demonstrate that the biphenol soft capsules were substantially the same as the "day 0" control in terms of appearance, disintegration time, and the content, indicating that the biphenol soft capsules are stable in quality under conditions of a high temperature, high humidity, and intense light.

2. Accelerated Test

Samples prepared according to Examples 1, 3, 5, 9, 11, and 14 were taken and placed at a temperature of 40° C.±2° C. and relative humidity of 75%±5% for 6 months to carry out an accelerated test. The results are shown below.

| Samples | Time (month) | Appearance of the contents in the capsule | Disintegration time (min) | Content (% of the labeled content) |
|---|---|---|---|---|
| Example 1 | 0 | Yellow oily liquid | 7.7 | 99.97 |
|  | 1 | Yellow oily liquid | 8.6 | 99.65 |
|  | 2 | Yellow oily liquid | 8.8 | 99.76 |
|  | 3 | Yellow oily liquid | 8.4 | 99.54 |
|  | 6 | Yellow oily liquid | 9.3 | 99.12 |
| Example 3 | 0 | Yellow oily liquid | 8.7 | 99.87 |
|  | 1 | Yellow oily liquid | 7.9 | 99.85 |
|  | 2 | Yellow oily liquid | 8.4 | 99.73 |
|  | 3 | Yellow oily liquid | 7.9 | 99.12 |
|  | 6 | Yellow oily liquid | 8.9 | 98.77 |
| Example 5 | 0 | Yellow oily liquid | 8.9 | 99.96 |
|  | 1 | Yellow oily liquid | 6.8 | 99.78 |
|  | 2 | Yellow oily liquid | 7.6 | 99.67 |
|  | 3 | Yellow oily liquid | 7.9 | 99.32 |
|  | 6 | Yellow oily liquid | 8.6 | 99.07 |
| Example 9 | 0 | Yellow oily liquid | 8.6 | 99.89 |
|  | 1 | Yellow oily liquid | 9.1 | 99.91 |
|  | 2 | Yellow oily liquid | 8.3 | 99.83 |
|  | 3 | Yellow oily liquid | 8.8 | 99.41 |
|  | 6 | Yellow oily liquid | 7.9 | 99.43 |
| Example 11 | 0 | Yellow oily liquid | 7.6 | 99.96 |
|  | 1 | Yellow oily liquid | 8.5 | 99.88 |
|  | 2 | Yellow oily liquid | 8.7 | 99.83 |
|  | 3 | Yellow oily liquid | 8.8 | 99.65 |
|  | 6 | Yellow oily liquid | 8.5 | 99.44 |
| Example 14 | 0 | Yellow oily liquid | 8.5 | 99.88 |
|  | 1 | Yellow oily liquid | 9.2 | 99.87 |
|  | 2 | Yellow oily liquid | 8.2 | 99.68 |
|  | 3 | Yellow oily liquid | 8.4 | 99.32 |
|  | 6 | Yellow oily liquid | 7.3 | 99.22 |

The above results demonstrate that the biphenol soft capsules were substantially the same as the "month 0" control in terms of appearance, disintegration time, and the content, indicating that the biphenol soft capsules are stable in quality.

3. Long-Term Test

Samples prepared according to Examples 1, 3, 5, 9, 11, and 14 were placed at a temperature of 25° C.±2° C. and relative humidity of 60%±10% for 12 months to carry out a long-term test. The results are shown below.

| Samples | Time (month) | Appearance of the contents in the capsule | Disintegration time (min) | Content (% of the labeled content) |
|---|---|---|---|---|
| Example 1 | 0 | Yellow oily liquid | 7.7 | 99.97 |
|  | 3 | Yellow oily liquid | 8.6 | 99.65 |
|  | 6 | Yellow oily liquid | 8.6 | 99.43 |
|  | 9 | Yellow oily liquid | 9.3 | 99.17 |
|  | 12 | Yellow oily liquid | 9.1 | 98.65 |
| Example 3 | 0 | Yellow oily liquid | 8.7 | 99.87 |
|  | 3 | Yellow oily liquid | 8.4 | 99.73 |
|  | 6 | Yellow oily liquid | 7.6 | 99.23 |
|  | 9 | Yellow oily liquid | 8.6 | 99.01 |
|  | 12 | Yellow oily liquid | 9.3 | 98.86 |
| Example 5 | 0 | Yellow oily liquid | 8.9 | 99.96 |
|  | 3 | Yellow oily liquid | 7.6 | 99.67 |
|  | 6 | Yellow oily liquid | 7.9 | 99.45 |
|  | 9 | Yellow oily liquid | 8.4 | 99.27 |
|  | 12 | Yellow oily liquid | 8.5 | 99.18 |
| Example 9 | 0 | Yellow oily liquid | 8.6 | 99.89 |
|  | 3 | Yellow oily liquid | 8.3 | 99.83 |
|  | 6 | Yellow oily liquid | 8.6 | 99.76 |
|  | 9 | Yellow oily liquid | 7.9 | 99.21 |
|  | 12 | Yellow oily liquid | 9.2 | 98.67 |
| Example 11 | 0 | Yellow oily liquid | 7.9 | 99.97 |
|  | 3 | Yellow oily liquid | 8.6 | 99.78 |
|  | 6 | Yellow oily liquid | 8.6 | 99.56 |
|  | 9 | Yellow oily liquid | 8.3 | 99.38 |
|  | 12 | Yellow oily liquid | 9.3 | 98.90 |
| Example 14 | 0 | Yellow oily liquid | 8.2 | 99.87 |

| Samples | Time (month) | Appearance of the contents in the capsule | Disintegration time (min) | Content (% of the labeled content) |
|---|---|---|---|---|
| | 3 | Yellow oily liquid | 8.4 | 99.76 |
| | 6 | Yellow oily liquid | 9.3 | 99.62 |
| | 9 | Yellow oily liquid | 8.8 | 99.39 |
| | 12 | Yellow oily liquid | 9.5 | 98.66 |

The above results demonstrate that the biphenol soft capsules were substantially the same as the "month 0" control in terms of appearance, disintegration time, and the content, indicating that the biphenol soft capsules are stable in quality.

Test Example 5. Pharmacodynamics Experiments

For the experiments, Kunming mice were divided into 5 groups, namely the model group, the control group (CMC-Na-biphenol group), dosed group 1, dosed group 2, and dosed group 3 (soft capsules prepared in accordance with Example 1 were selected for each dosed group), with 20 mice per group.

1. Pharmacodynamics Experiments to Test the Effect of Soft Capsules with Various Concentrations of Biphenol in Combating Pentylenetetrazole (PTZ)-Induced Epilepsy in Mice.

The experiments were performed on 5 groups, for which the route of administration, the dosed agent, and the dosage are shown in the table below. 2 hours after administration, PTZ (75 mg/kg) was injected intraperitoneally to establish models. The results are shown below.

| Groups | Route of administration | Dosed agent | Dosage (mg/kg) | Seizure grade | | | | | | Percentage of the effective (≤III) |
|---|---|---|---|---|---|---|---|---|---|---|
| | | | | 0 | I | II | III | IV | V | |
| Model group (n = 20) | Intragastric | Solution of contents in Blank Soft Capsule | equal volume | 0 | 0 | 0 | 0 | 18 | 2 | 0 |
| Control group (n = 20) | Intragastric | CMC-Na-Biphenol | 200 | 0 | 0 | 2 | 3 | 15 | 0 | 25% |
| Dosed group 1 (n = 20) | Intragastric | Solution of contents in Biphenol Soft Capsule | 200 | 20 | 0 | 0 | 0 | 0 | 0 | 100% |
| Dosed group 2 (n = 20) | Intragastric | Solution of contents in Biphenol Soft Capsule | 100 | 17 | 3 | 0 | 0 | 0 | 0 | 100% |
| Dosed group 3 (n = 20) | Intragastric | Solution of contents in Biphenol Soft Capsule | 50 | 14 | 3 | 3 | 0 | 0 | 0 | 100% |

The seizure grades were estimated for epilepsy animal models according to Racine's standard scale (Grade 0: no reaction; Grade I: rhythmic mouth and facial clonus; Grade II: head nodding or tail flicking; Grade III: jerks in one limb; Grade IV: tonic seizure or jerks in more limbs; Grade V: generalized tonic-clonic seizure).

2. Pharmacodynamics Experiments to Test the Effect of Soft Capsules with Various Concentrations of Biphenol in Combating Bicuculline-Induced Epilepsy in Mice.

The experiments were performed on 5 groups, for which the route of administration, the dosed agent, and the dosage are shown in the table below. 2 hours after administration, Bic (2.7 mg/kg) was injected subcutaneously to establish models. The results are shown below.

| Groups | Route of administration | Dosed agent | Dosage (mg/kg) | Seizure grade | | | | | | Percentage of the effective (≤IV) |
|---|---|---|---|---|---|---|---|---|---|---|
| | | | | 0 | I | II | III | IV | V | |
| Model group (n = 20) | Intragastric | Solution of contents in Blank Soft Capsule | equal volume | 0 | 0 | 0 | 0 | 0 | 20 | 0 |
| Control group (n = 20) | Intragastric | CMCNa-Biphenol | 200 | 0 | 0 | 2 | 4 | 2 | 14 | 30% |
| Dosed group 1 | Intragastric | Solution of contents in | 200 | 20 | 0 | 0 | 0 | 0 | 0 | 100% |

-continued

| Groups | Route of administration | Dosed agent | Dosage (mg/kg) | 0 | I | II | III | IV | V | Percentage of the effective (≤IV) |
|---|---|---|---|---|---|---|---|---|---|---|
| (n = 20) | | Biphenol Soft Capsule | | | | | | | | |
| Dosed group 2 (n = 20) | Intragastric | Solution of contents in Biphenol Soft Capsule | 100 | 15 | 3 | 2 | 0 | 0 | 0 | 100% |
| Dosed group 3 (n = 20) | Intragastric | Solution of contents in Biphenol Soft Capsule | 50 | 12 | 3 | 3 | 2 | 0 | 0 | 100% |

Evaluation criteria for the bicuculline (Bic) model: since this model leads to a 100% mortality rate, any survival after administration indicates effectiveness.

3. Pharmacodynamics Experiments to Test the Effect of Soft Capsules with Various Concentrations of Biphenol in Combating 3-Mercaptopropionic Acid-Induced Epilepsy in Mice.

The experiments were performed on 5 groups, for which the route of administration, the dosed agent, and the dosage are shown in the table below. 2 hours after administration, 3-MP (60 mg/kg) was injected subcutaneously to establish models. The results are shown below.

| Groups | Route of administration | Dosed agent | Dosage (mg/kg) | 0 | I | II | III | Percentage of the effective (≤III) |
|---|---|---|---|---|---|---|---|---|
| Model group (n = 20) | Intragastric | Solution of contents in Blank Soft Capsule | equal volume | 0 | 0 | 0 | 20 | 0% |
| Control group (n = 20) | Intragastric | CMCNa-Biphenol | 200 | 1 | 1 | 3 | 15 | 25% |
| Dosed group 1 (n = 20) | Intragastric | Solution of contents in Biphenol Soft Capsule | 200 | 20 | 0 | 0 | 0 | 100% |
| Dosed group 2 (n = 20) | Intragastric | Solution of contents in Biphenol Soft Capsule | 100 | 20 | 0 | 0 | 0 | 100% |
| Dosed group 3 (n = 20) | Intragastric | Solution of contents in Biphenol Soft Capsule | 50 | 18 | 1 | 1 | 0 | 100% |

Evaluation criteria for the 3-mercaptopropionic acid (3-MP) model: Grade I, latent period; Grade II: clonic convulsive seizures (clonic forelimb); Grade III: tonic convulsive seizures (tonic hindlimb).

4. Pharmacodynamics Experiments to Test the Effect of Soft Capsules with Various Concentrations of Biphenol in Combating Electric Shock-Induced Epilepsy in Mice.

The experiments were performed on 5 groups, for which the route of administration, the dosed agent, and the dosage are shown in the table below. 2 hours after administration, MES was applied to establish models. The results are shown below.

| Groups | Route of administration | Dosed agent | Dosage (mg/kg) | Seizure grade without seizure | with seizure | Percentage of the effective |
|---|---|---|---|---|---|---|
| Model group (n = 20) | Intragastric | Solution of contents in Blank Soft Capsule | equal volume | 0 | 20 | 0% |

-continued

| Groups | Route of administration | Dosed agent | Dosage (mg/kg) | Seizure grade without seizure | Seizure grade with seizure | Percentage of the effective |
|---|---|---|---|---|---|---|
| Control group (n = 20) | Intragastric | CMCNa-Biphenol | 200 | 3 | 17 | 15% |
| Dosed group 1 (n = 20) | Intragastric | Solution of contents in Biphenol Soft Capsule | 200 | 17 | 3 | 85% |
| Dosed group 2 (n = 20) | Intragastric | Solution of contents in Biphenol Soft Capsule | 100 | 14 | 6 | 70% |
| Dosed group 3 (n = 20) | Intragastric | Solution of contents in Biphenol Soft Capsule | 50 | 12 | 8 | 60% |

Evaluation criteria for the electric shock (MES) model: presence or absence of tonic limbs in the animals is regarded as seizure or no seizure.

5. Pharmacodynamics Experiments to Test the Effect of Soft Capsules with Various Concentrations of Biphenol in Combating Penicillin-Induced Epilepsy in Mice.

The experiments were performed on 5 groups, for which the route of administration, the dosed agent, and the dosage are shown in the table below. 2 hours after administration, penicillin (6 million U/kg) was injected intraperitoneally to establish models. The results are shown below.

| Groups | Route of administration | Dosed agent | Dosage (mg/kg) | Seizure grade 0 | I | II | III | IV | V | Percentage of the effective (≤III) |
|---|---|---|---|---|---|---|---|---|---|---|
| Model group (n = 20) | Intragastric | Solution of contents in Blank Soft Capsule | equal volume | 0 | 0 | 0 | 0 | 16 | 4 | 0 |
| Control group (n = 20) | Intragastric | CMCNa-Biphenol | 200 | 0 | 0 | 2 | 2 | 16 | 0 | 20% |
| Dosed group 1 (n = 20) | Intragastric | Solution of contents in Biphenol Soft Capsule | 200 | 18 | 1 | 1 | 0 | 0 | 0 | 100% |
| Dosed group 2 (n = 20) | Intragastric | Solution of contents in Biphenol Soft Capsule | 100 | 15 | 2 | 2 | 1 | 0 | 0 | 100% |
| Dosed group 3 (n = 20) | Intragastric | Solution of contents in Biphenol Soft Capsule | 50 | 12 | 3 | 1 | 2 | 2 | 0 | 90% |

The seizure grades upon penicillin induction were estimated for epilepsy animal models according to Racine's standard scale (Grade 0: no reaction; Grade I: rhythmic mouth and facial clonus; Grade II: head nodding or tail flicking; Grade III: jerks in one limb; Grade IV: tonic seizure or jerks in more limbs; Grade V: generalized tonic-clonic seizure).

The experimental results demonstrate that biphenol soft capsules showed a several-fold increase in drug efficacy as compared to CMC-Na-biphenol, indicating that dissolving biphenol in the formula oils in accordance with the present invention improves drug absorption and significantly enhances the therapeutic effect.

Comparative Examples 1-8

| Ingredients | Comp. Ex. 1 | Comp. Ex. 2 | Comp. Ex. 3 | Comp. Ex. 4 | Comp. Ex. 5 | Comp. Ex. 5 | Comp. Ex. 7 | Comp. Ex. 8 |
|---|---|---|---|---|---|---|---|---|
| Biphenol | 100 | 100 | 100 | 100 | 100 | 100 | 100 | 100 |
| Inositol | 50 | | | | 50 | | | |
| Malic acid | | 50 | | | | 50 | | |
| Butyl hydroxyanisole | | | 50 | | | | 50 | |
| Propyl gallate | | | | 50 | | | | 50 |
| Soybean oil | 350 | | | | | | | 350 |
| Corn oil | | 350 | | | 350 | | | |
| Safflower oil | | | 350 | | | | 350 | |
| Perilla oil | | | | 350 | | 350 | | |

Comparative examples 1-4 followed the same preparation process as that in Example 1; and Comparative examples 5-8 followed the same preparation process as that in Example 2.

Tests for Comparison of Stability

Samples prepared according to Examples 1, 2, 5, 6, 9, 10, 12 and 13 and Comparative examples 1-8 were taken and placed at a temperature of 40° C.±2° C. and relative humidity of 75%±5% for 6 months to carry out an accelerated test. The results are shown below.

| Samples | Time (month) | Appearance of the contents in the capsule | Disintegration time (min) | Content (% of the labeled content) |
|---|---|---|---|---|
| Example 1 | 0 | Yellow oily liquid | 7.8 | 99.87 |
| | 1 | Yellow oily liquid | 7.6 | 99.75 |
| | 2 | Yellow oily liquid | 8.3 | 99.67 |
| | 3 | Yellow oily liquid | 8.1 | 99.45 |
| | 6 | Yellow oily liquid | 8.3 | 99.13 |
| Example 2 | 0 | Yellow oily liquid | 7.7 | 99.97 |
| | 1 | Yellow oily liquid | 8.1 | 99.91 |
| | 2 | Yellow oily liquid | 8.5 | 99.82 |
| | 3 | Yellow oily liquid | 8.4 | 99.55 |
| | 6 | Yellow oily liquid | 9.1 | 98.37 |
| Example 5 | 0 | Yellow oily liquid | 8.5 | 99.88 |
| | 1 | Yellow oily liquid | 7.1 | 99.74 |
| | 2 | Yellow oily liquid | 7.3 | 99.61 |
| | 3 | Yellow oily liquid | 7.7 | 99.55 |
| | 6 | Yellow oily liquid | 8.2 | 99.17 |
| Example 6 | 0 | Yellow oily liquid | 8.3 | 99.94 |
| | 1 | Yellow oily liquid | 9.3 | 99.88 |
| | 2 | Yellow oily liquid | 7.5 | 99.73 |
| | 3 | Yellow oily liquid | 8.2 | 99.34 |
| | 6 | Yellow oily liquid | 7.5 | 99.32 |
| Example 9 | 0 | Yellow oily liquid | 8.2 | 99.83 |
| | 1 | Yellow oily liquid | 8.4 | 99.82 |
| | 2 | Yellow oily liquid | 8.9 | 99.69 |
| | 3 | Yellow oily liquid | 8.7 | 99.66 |
| | 6 | Yellow oily liquid | 8.4 | 99.23 |
| Example 10 | 0 | Yellow oily liquid | 7.8 | 99.97 |
| | 1 | Yellow oily liquid | 8.2 | 99.82 |
| | 2 | Yellow oily liquid | 8.3 | 99.76 |
| | 3 | Yellow oily liquid | 9.2 | 99.69 |
| | 6 | Yellow oily liquid | 8.9 | 99.42 |
| Example 12 | 0 | Yellow oily liquid | 8.6 | 99.83 |
| | 1 | Yellow oily liquid | 8.4 | 99.81 |
| | 2 | Yellow oily liquid | 8.9 | 99.64 |
| | 3 | Yellow oily liquid | 8.4 | 99.45 |
| | 6 | Yellow oily liquid | 9.3 | 99.12 |
| Example 13 | 0 | Yellow oily liquid | 8.3 | 99.85 |
| | 1 | Yellow oily liquid | 7.8 | 99.78 |
| | 2 | Yellow oily liquid | 8.4 | 99.56 |
| | 3 | Yellow oily liquid | 8.8 | 99.47 |
| | 6 | Yellow oily liquid | 9.1 | 99.04 |
| Comp. Ex. 1 | 0 | Yellow oily liquid | 8.3 | 99.98 |
| | 1 | Yellow oily liquid | 7.7 | 99.75 |
| | 2 | Yellow oily liquid | 8.5 | 99.32 |
| | 3 | Yellow oily liquid | 8.3 | 98.92 |
| | 6 | Yellow oily liquid | 8.6 | 97.01 |
| Comp. Ex. 2 | 0 | Yellow oily liquid | 8.7 | 99.86 |
| | 1 | Yellow oily liquid | 8.4 | 99.54 |
| | 2 | Yellow oily liquid | 7.6 | 99.13 |
| | 3 | Yellow oily liquid | 8.6 | 98.42 |
| | 6 | Yellow oily liquid | 7.8 | 96.26 |
| Comp. Ex. 3 | 0 | Yellow oily liquid | 7.6 | 99.93 |
| | 1 | Yellow oily liquid | 8.8 | 99.44 |
| | 2 | Yellow oily liquid | 8.3 | 99.25 |
| | 3 | Yellow oily liquid | 8.9 | 98.76 |
| | 6 | Yellow oily liquid | 8.4 | 98.18 |
| Comp. Ex. 4 | 0 | Yellow oily liquid | 7.8 | 99.79 |
| | 1 | Yellow oily liquid | 8.4 | 98.88 |
| | 2 | Yellow oily liquid | 8.9 | 98.64 |
| | 3 | Yellow oily liquid | 9.3 | 97.37 |
| | 6 | Yellow oily liquid | 8.7 | 95.96 |
| Comp. Ex. 5 | 0 | Yellow oily liquid | 8.3 | 99.76 |
| | 1 | Yellow oily liquid | 7.7 | 99.17 |
| | 2 | Yellow oily liquid | 8.6 | 98.45 |
| | 3 | Yellow oily liquid | 8.5 | 98.12 |
| | 6 | Yellow oily liquid | 8.3 | 97.09 |
| Comp. Ex. 6 | 0 | Yellow oily liquid | 7.6 | 99.88 |
| | 1 | Yellow oily liquid | 8.7 | 99.87 |
| | 2 | Yellow oily liquid | 8.1 | 99.68 |
| | 3 | Yellow oily liquid | 8.0 | 99.32 |
| | 6 | Yellow oily liquid | 8.2 | 99.22 |
| Comp. Ex. 7 | 0 | Yellow oily liquid | 8.1 | 99.89 |
| | 1 | Yellow oily liquid | 8.7 | 99.65 |
| | 2 | Yellow oily liquid | 8.9 | 99.11 |
| | 3 | Yellow oily liquid | 9.1 | 98.56 |
| | 6 | Yellow oily liquid | 9.2 | 98.02 |
| Comp. Ex. 8 | 0 | Yellow oily liquid | 8.1 | 99.78 |
| | 1 | Yellow oily liquid | 8.2 | 99.18 |
| | 2 | Yellow oily liquid | 7.5 | 98.26 |
| | 3 | Yellow oily liquid | 8.6 | 97.23 |
| | 6 | Yellow oily liquid | 9.3 | 96.66 |

The results demonstrate that the biphenol soft capsules of the Examples had the same appearance and disintegration time as those of the Comparative examples, but showed significantly higher stability in content than the Comparative examples, indicating the formulation and process used in accordance with the present invention further stabilize the quality of biphenol soft capsules.

Experiments for Comparison of Pharmacodynamics

Samples prepared according to Examples 1, 2, 5, 6, 9, 10, 12 and 13 and Comparative examples 1-8 were taken and tested for their drug efficacy on PTZ-induced epilepsy in mice. The experiments were performed on 17 groups, for which the route of administration, the dosed agent, and the dosage are shown in the table below. 2 hours after administration, PTZ (75 mg/kg) was injected intraperitoneally to establish models. The results are shown below.

| Groups | Route of administration | Dosed agent | Dosage (mg/kg) | Seizure grade | | | | | | Percentage of the effective (≤III) |
|---|---|---|---|---|---|---|---|---|---|---|
| | | | | 0 | I | II | III | IV | V | |
| Model group (n = 20) | Intragastric | Solution of contents in Blank Soft Capsule | equal volume | 0 | 0 | 0 | 0 | 17 | 3 | 0 |
| Example 1 (n = 20) | Intragastric | Solution of contents in Biphenol Soft Capsule | 200 | 19 | 0 | 1 | 0 | 0 | 0 | 100% |
| Example 2 (n = 20) | Intragastric | Solution of contents in Biphenol Soft Capsule | 200 | 18 | 1 | 1 | 0 | 0 | 0 | 100% |
| Example 5 (n = 20) | Intragastric | Solution of contents in Biphenol Soft Capsule | 200 | 17 | 3 | 0 | 0 | 0 | 0 | 100% |
| Example 6 (n = 20) | Intragastric | Solution of contents in Biphenol Soft Capsule | 200 | 18 | 0 | 2 | 0 | 0 | 0 | 100% |
| Example 9 (n = 20) | Intragastric | Solution of contents in Biphenol Soft Capsule | 200 | 17 | 1 | 1 | 1 | 0 | 0 | 100% |
| Example 10 (n = 20) | Intragastric | Solution of contents in Biphenol Soft Capsule | 200 | 18 | 2 | 0 | 0 | 0 | 0 | 100% |
| Example 12 (n = 20) | Intragastric | Solution of contents in Biphenol Soft Capsule | 200 | 16 | 1 | 2 | 1 | 0 | 0 | 100% |
| Example 13 (n = 20) | Intragastric | Solution of contents in Biphenol Soft Capsule | 200 | 17 | 1 | 2 | 0 | 0 | 0 | 100% |
| Comp. Ex. 1 (n = 20) | Intragastric | Solution of contents in Biphenol Soft Capsule | 200 | 12 | 2 | 1 | 3 | 2 | 0 | 90% |
| Comp. Ex. 2 (n = 20) | Intragastric | Solution of contents in Biphenol Soft Capsule | 200 | 13 | 1 | 2 | 1 | 3 | 0 | 85% |
| Comp. Ex. 3 (n = 20) | Intragastric | Solution of contents in Biphenol Soft Capsule | 200 | 14 | 2 | 2 | 1 | 1 | 0 | 95% |
| Comp. Ex. 4 (n = 20) | Intragastric | Solution of contents in Biphenol Soft Capsule | 200 | 11 | 1 | 3 | 2 | 3 | 0 | 85% |
| Comp. Ex. 5 (n = 20) | Intragastric | Solution of contents in Biphenol Soft Capsule | 200 | 11 | 2 | 3 | 1 | 3 | 0 | 85% |
| Comp. Ex. 6 (n = 20) | Intragastric | Solution of contents in Biphenol Soft Capsule | 200 | 10 | 3 | 1 | 2 | 4 | 0 | 80% |
| Comp. Ex. 7 (n = 20) | Intragastric | Solution of contents in Biphenol Soft Capsule | 200 | 15 | 1 | 2 | 1 | 1 | 0 | 95% |
| Comp. Ex. 8 (n = 20) | Intragastric | Solution of contents in Biphenol Soft Capsule | 200 | 12 | 2 | 1 | 2 | 3 | 0 | 85% |

The seizure grades were estimated for epilepsy animal models according to Racine's standard scale (Grade 0: no reaction; Grade I: rhythmic mouth and facial clonus; Grade II: head nodding or tail flicking; Grade III: jerks in one limb; Grade IV: tonic seizure or jerks in more limbs; Grade V: generalized tonic-clonic seizure).

The experimental results demonstrate that all of the biphenol soft capsules prepared in accordance with the Examples showed better drug efficacy than that of the Comparative Examples.

The invention claimed is:

1. A soft capsule of 2,2',6,6'-tetraisopropyl-4,4'-biphenol, characterized in that the contents encapsulated in the soft capsule comprise: 1% to 30% of 2,2',6,6'-tetraisopropyl-4,4'-biphenol and 5% to 10% of vitamin E, based on the total contents in the capsule.

2. The soft capsule according to claim 1, characterized in that the vitamin E is one or more of tocopheryl acetate, tocotrienol, tocopherol, and derivatives of tocotrienol.

3. A soft capsule of 2,2',6,6'-tetraisopropyl-4,4'-biphenol, characterized in that the contents encapsulated in the soft capsule comprise the following components:
   1% to 30% of 2,2',6,6'-tetraisopropyl-4,4'-biphenol,
   60% to 90% of a dispersant,
   5% to 10% of vitamin E,
   0% to 0.3% of a preservative,
   on the basis of the total contents in the capsule.

4. The soft capsule according to claim 3, characterized in that the dispersant is one selected from the group consisting of vegetable oils, medium-chain oils, structured oils, and a mixture of at least two of them, and the vegetable oils are selected from the group consisting of *Perilla* oil, cottonseed oil, olive oil, linolenic acid, soybean oil, peanut oil, safflower oil, and corn oil.

5. The soft capsule according to claim 1, characterized in that the capsule shell is composed of a gel material, a plasticizer, and a solvent, wherein the gel material is selected from the group consisting of arabic gum, carrageenan, and gelatin; the plasticizer is one or more selected from the group consisting of glycerol, xylitol, sorbitol, and methyl sorbate; the solvent is selected from the group consisting of water; and the weight ratio between the components in the capsule shell is gel material:plasticizer:water=1:0.3 to 0.6:1.

6. A method for treating epileptic symptoms comprising administering a soft capsule of 2,2',6,6'-tetraisopropyl-4,4'-biphenol of claim 1.

7. The method of claim 6, wherein the epileptic symptoms include generalized tonic-clonic seizures, absence seizures, simple partial seizures, complex partial seizures, and autonomic seizures.

* * * * *